United States Patent

Iwakuma et al.

[11] Patent Number: 4,579,854
[45] Date of Patent: Apr. 1, 1986

[54] BRONCHODILATING 8-HYDROXY-5-{(1R)-1-HYDROXY-2-[N-((1R)-2-(P-METHOXYPHENYL)-1-METHYLETHYL)-AMINO]ETHYL} CARBOSTYRIL

[75] Inventors: Takeo Iwakuma, Ageo; Akira Tsunashima, Toda; Katsuo Ikezawa, Urawa; Osasi Takaiti, Shiki, all of Japan

[73] Assignee: Tanabe Seiyaku Co., Ltd., Japan

[21] Appl. No.: 684,505

[22] Filed: Dec. 21, 1984

[30] Foreign Application Priority Data

Dec. 24, 1983 [GB] United Kingdom ................ 8334494

[51] Int. Cl.$^4$ ..................... A61K 31/47; C07D 215/22
[52] U.S. Cl. ........................................ 514/312; 546/157
[58] Field of Search ....................... 546/157; 424/258; 514/312

[56] References Cited

U.S. PATENT DOCUMENTS 4,022,776  5/1977  Nakagawa ............................ 546/157
4,223,137  9/1980  Yoshizaki ............................ 546/158

FOREIGN PATENT DOCUMENTS 13510  3/1984  Japan ..................... 546/157

Primary Examiner—Donald G. Daus
Assistant Examiner—Robert Benson
Attorney, Agent, or Firm—Scully, Scott Murphy & Presser

[57] ABSTRACT

A novel carbostyril derivative of the formula:

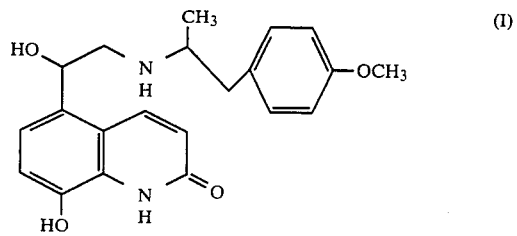

or a pharmaceutically acceptable acid addition salt thereof, and a process for preparing same. The compound (I) shows potent bronchodilating activity and is useful as a bronchodilator.

5 Claims, No Drawings

BRONCHODILATING 8-HYDROXY-5-{(1R)-1-HYDROXY-2-[N-((1R)-2-(P-METHOXYPHENYL)-1-METHYLETHYL)-AMINO]ETHYL} CARBOSTYRIL

This invention relates to a novel carbostyril derivative and a process for preparing same. More particularly, it relates to a compound of the formula:

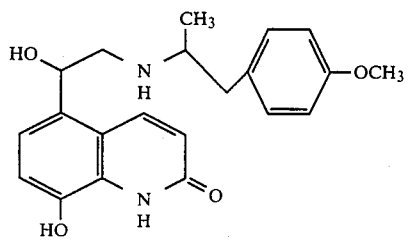

(I)

or a pharmaceutically acceptable acid addition salt thereof.

The carbostyril derivative (I) or a pharmaceutically acceptable acid addition salt thereof shows potent $\beta_2$-adrenoceptor stimulating action and is useful as a bronchodilator.

The comound (I) of the present invention can exist in the form of four optical isomes (i.e., (R) (R)-, (R) (S)-, (S) (R)- and (S) (S)-isomers) due to the two asymmetric carbon atoms involved in the side chain:

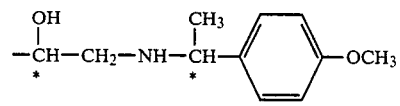

wherein the asterisk denotes an asymmetric carbon atom. The present invention includes within its scope all of four optical isomers and mixtures thereof.

Throughout the specification, the terms "(R) (R)-isomer", "(R) (S)-isomer", "(S) (R)-isomer" and (S) (S)-isomer" mean the configuration of the asymmetric carbon atoms at the position of —CH(OH)— and that of —CH(CH₃)—, respectively. Therefore, for example, "(S) (R)-isomer" means that the asymmetric carbon atom at the position of —CH(OH)— has (S)-configuration and the asymmetric carbon atom at the position of —CH(CH₃)— has (R)-configuration. Further, throughout the specification, the term "α-isomer" means a stereoisomer which is a mixture of (R) (R)- and (S) (S)-isomers, and the term "β-isomer" means a stereoisomer which is a mixture of (R) (S)- and (S) (R)-isomers. Besides, the compound of the present invention has the following two tautomeric structures which are mutually convertible from one to another. Both of these isomers are also included within the scope of the present invention.

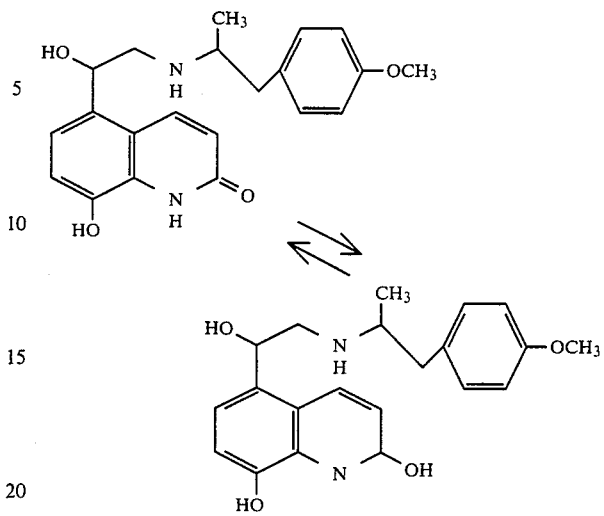

According to the present invention, the compound (I) is prepared by reducing a compound of the formula:

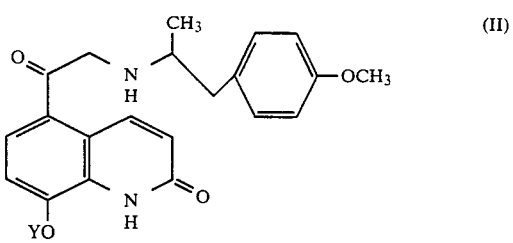

(II)

or

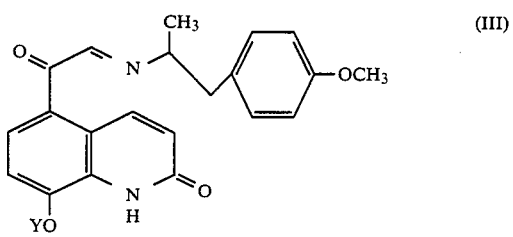

(III)

wherein YO— is hydroxy or a protected hydroxy, to give a compound of the formula:

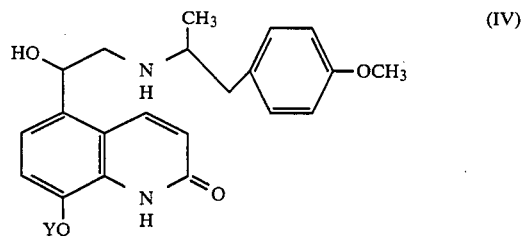

(IV)

wherein YO— is the same as defined above, and when YO- is a protected hydroxy, further removing the protecting group therefrom.

In the above-mentioned reactions, a wide variety of protecting groups which have been usually employed to protect hydroxy group can be used as the protecting group (Y). Examples of such protecting group include lower alkanoyl such as formyl, acetyl and pivaloyl; substituted or unsubstituted phenyl-lower alkyl such as benzyl, p-methoxybenzyl and 3,4-dimethoxybenzyl; substituted or unsubstituted benzyloxycarbonyl such as benzyloxycarbonyl and p-methoxybenzyloxycarbonyl; or substituted or unsubstituted phenylsulfonyl such as benzenesulfonyl and p-toluenesulfonyl.

The reduction of the compound (II) or (III) can be accomplished by reacting it with a reducing agent in a solvent. Suitable examples of the reducing agent include sodium borohydride, lithium aluminium hydride, lithium borohydride, sodium monoacetoxyborohydride, diborane or sodium cyanoborohydride. Methanol, ethanol, isopropanol, dimethylformamide, dimethylsulfoxide, tetrahydrofuran, ether, dimethoxyethane, diglyme, dioxane, toluene or a mixture thereof is suitable as the solvent. It is preferred to carry out the reaction at a temperature of −20° to 30° C.

On the other hand, the subsequent removal of the protecting group can be conducted by conventional manners such as, for example, hydrolysis, organic base treatment or reduction. For example, when the protecting group is formyl, acetyl or benzenesulfonyl, said group may be removed by hydrolysis of the compound (IV) with an acid or an akali. Suitable examples of such acid include, for example, formic acid, trifluoroacetic acid, benzenesulfonic acid, p-toluenesulfonic acid, hydrochloric acid or hydrobromic acid. Suitable examples of such alkali include, for example, sodium carbonate, potassium carbonate, sodium hydroxide or potassium hydroxide. This reaction may be conducted with or without a solvent. Examples of the solvent are water, methanol, ethanol or dioxane. It is preferred to carry out the reaction at a temperature of −30° to 70° C., especially 20° to 50° C. When the protecting group is benzyl, p-methoxybenzyl, 3,4-dimethoxybenzyl, benzyloxycarbonyl or p-methoxybenzyloxycarbonyl, the removal of said protecting group may be conducted by catalytic hydrogenation of the compound (IV) in hydrogen gas in the presence of a catalyst. This catalytic hydrogenation is preferably carried out at a temperature of 0° to 100° C., especially 20° to 40° C., under atmospheric or increased pressure. Preferred examples of the catalyst include palladium-BaCO3, palladium-charcoal and palladium-black. Methanol, ethanol, tetrahydrofuran, water or a mixture thereof is suitable as the reaction solvent. Further, when the protecting group is acetyl or pivaloyl, said group may be removed by the treatment of the compound (IV) with an organic base. The treatment of the compound (IV) can be carried out in conventional manners, for example, by treating it with an organic base such as methylamine, dimethylamine, ethylamine or diethylamine. This reaction may be conducted with or without a solvent. Examples of the solvent are water, methanol, ethanol, dioxane or a mixture thereof. It is preferred to carry out the reaction at a temperature of 0° to 100° C., especially 20° to 70° C.

When a racemic modification of the compound (II) or (III) (YO—=a protected hydroxy) is used as the starting compound in the above-mentioned reaction, the compound (IV) in which YO— is a protected hydroxy, i.e., a compound of the formula:

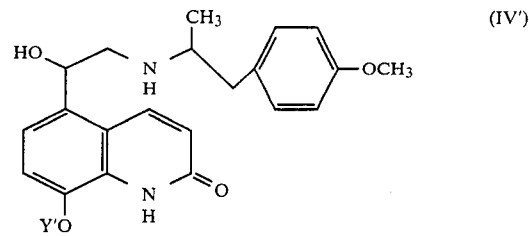

wherein Y'O— is a protected hydroxy, is obtained in the form of a mixture of two stereoisomers (i.e., α- and β-isomers) and may be, if required, separated into each of the stereoisomers prior to removal of the protecting group (Y') therefrom. For example, each one of the α- and β-isomers of the compound (IV') may be obtained by acylating the compound (IV') to give a compound of the formula:

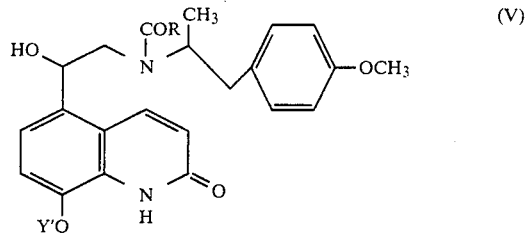

wherein RCO— is an acyl group and Y'O— is the same as defined above, subjecting said compound (V) to chromatography to separate it into each of α- and β-isomers thereof, and then removing the acyl group therefrom. The acylating agent which is used for acylation of the compound (IV') includes, for example, acetyl chloride, acetyl bromide, chloroacetyl chloride, p-nitrobenzoyl chloride, and the like. The acylation is preferably carried out in the presence of an acid acceptor (e.g., sodium hydroxide, potassium hydroxide, sodium carbonate, potassium carbonate, sodium bicarbonate, potassium bicarbonate) in a solvent (e.g., ethyl acetate, methylene chloride, chloroform, benzene, water or a mixture thereof) at a temperature of 0° to 30° C. Subsequent chromatographic separation of α- and β-isomers of the compound (V) can be effected on a column of silica gel, using meathanol, chloroform, methylene chloride, ethyl acetate, benzene, n-hexane or a mixture thereof as an eluent. Then, the removal of the acyl group from the thus-separated each stereoisomer (α- or β-isomer) of the compound (V) can be accomplished by conventional hydrolysis thereof, for example, by treating said isomer with a base (e.g., potassium hydroxide, sodium hydroxide, potassium carbonate, sodium carbonate) or an acid (e.g., hydrochloric acid, sulfuric acid, nitric acid) in a solvent (e.g., water, aqueous methanol, aqueous ethanol) at a temperature of 20° to 100° C.

The α- or β-isomer of the compound (IV') obtained above (i.e., a mixture of (R) (R)- and (S) (S)-isomers thereof or a mixture of (R) (S)- and (S) (R)-isomers thereof) may be, if required, further separated into each of the optical isomers of the compound (IV'). For example, each one of (R) (R)- and (S) (S)-isomers of the compound (IV') may be obtained by acylating the α-isomer of the compound (IV') with an optically active acylating agent to give a compound of the formula:

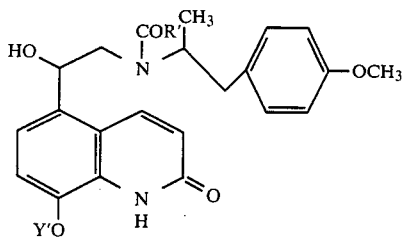

(V')

wherein R'CO- is an optically active acyl group and Y'O— is the same as defined above, subjecting the compound (V') to chromatography to separate it into each of (R) (R)- and (S) (S)-isomers of the compound (V'), and then removing the acyl group therefrom. The optically active acylating agent which is used for acylation of the compound (IV') includes, for example, an optically active 1-(2-naphthylsulfonyl)pyrrolidine-2-carbonyl chloride. The acylation of the compound (IV') is carried out in the presence of an acid acceptor (e.g., sodium hydroxide, potassium hydroxide, sodium carbonate, potassium carbonate, sodium bicarbonate, potassium bicarbonate) in a solvent (e.g., ethyl acetate, methylene chloride, chloroform, benzene, water or a mixture thereof) at a temperature of 0° to 30° C. Subsequent chromatographic separation of the (R) (R)- and (S) (S)-isomers of the compound (V') and the removal of the acyl group therefrom may be carried out in the same manner as mentioned hereinbefore. Each one of (R) (S)- and (S) (R)-isomer of the compound (IV') may be obtained from the β-isomer of the compound (IV') in the same manner as above.

On the other hand, the compound (IV') which is prepared from an optical isomer of the compound (II) or (III) (YO——=a protected hydroxy) is a mixture of two optical isomers thereof which are a pair of diastereoisomers. For example, a mixture of (R) (R)- and (S) (R)-isomers of the compound (IV') is obtained when the (R)-isomer of the compound (II) or (III) (YO——=a protected hydroxy) is used as the starting compound, while a mixture of (R) (S)- and (S) (S)-isomers of the compound (IV') is obtained when the (S)-isomer of the compound (II) or (III) (YO——=a protected hydroxy) is used as the starting compound. However, said mixture may be, if required, separated into each of the two optical isomers of the compound (IV') prior to removal of the protecting group (Y') therefrom. For example, each one of the (R) (R)- and (S) (R)-isomers of the compound (IV') may be obtained by subjecting the compound (IV') to fractional recrystallization; or by acylating the compound (IV') to give the compound (V), subjecting the compound (V) to chromatography to separate it into each of (R) (R)- and (S) (R)-isomers of the compound (V), and then removing the acyl group therefrom. The fractional recrystallization is carried out by recrystallizing the compound (IV') from a solvent (e.g., methanol, ethanol, isopropanol, water or a mixture thereof). The acylation of the compound (IV'), the chromatographic separation and the removal of the acyl group may be carried out in the same manner as described hereinbefore. Each one of the (R) (S)- and (S) (S)-isomers of the compound (IV') may be obtained in the same manner as above.

Moreover, since the β-isomer (or α-isomer) of the compound (V) separated above can be readily converted into the α-isomer (or β-isomer) of the compound (IV'), the compound (IV') may be, if required, recovered exclusively in the form of either the α- or β-isomer thereof. For example, the conversion of the β-isomer of the compound (V) into the α-isomer of the compound (IV') is carried out by treating said β-isomer with thionyl chloride in a solvent (e.g., methylene chloride, chloroform, benzene, toluene, tetrahydrofuran, dioxane or dimethoxyethane) to give an α-isomer of a compound of the formula:

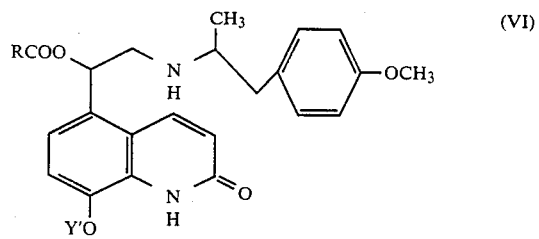

(VI)

wherein RCO— and Y'O— are the same as defined above, and then removing the acyl group therefrom. The conversion of the α-isomer of the compound (V) into the β-isomer of the compound (IV') may be carried out in the same manner as above.

Furthermore, the optical isomer of the compound (V) separated above can be readily converted into an optical isomer of the compound (IV') in which the asymmetric carbon atom at the position of —CH(OH)— has the opposite configuration from that of the former optical isomer. For example, the conversion of the (S) (R)-isomer of the compound (V) into the (R) (R)-isomer of the compound (IV') is carried out by treating the compound (V) with thionyl chloride in a solvent (e.g., methylene chloride, chloroform, benzene, toluene, tetrahydrofuran, dioxane or dimethoxyethane) to give the (R) (R)-isomer of the compound (VI), and then removing the acyl group therefrom. The conversion of the (R) (R)-, (R) (S)- or (S) (S)-isomer of the compound (V) into the (S) (R)-, (S) (S)- or (R) (S)-isomer of the compound (IV') may be respectively carried out in the same manner as above.

The starting compound (II) and (III) of the present invention is a novel compound and can be prepared, for exampe, by the steps of halogenating or oxidizing a compound of the formula:

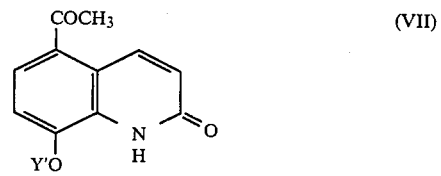

(VII)

wherein Y'O— is the same as defined above, to give a compound of the formula:

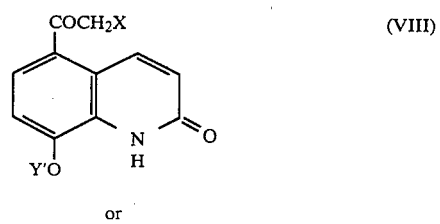

(VIII)

or

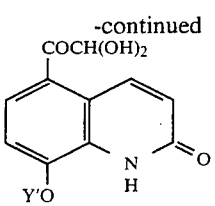

(IX)

wherein X is halogen atom and Y'O— is the same as defined above, reacting the compound (VIII) or (IX) with a compound of the formula:

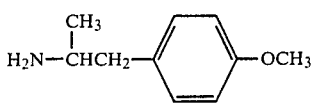

(X)

to give a compound of the formula:

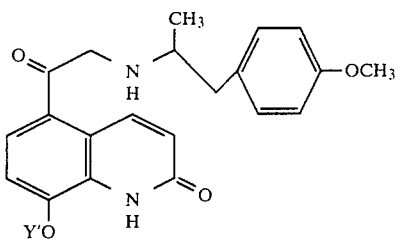

(II')

or

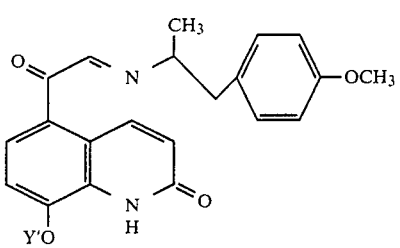

(III')

wherein Y'O— is the same as defined above, and if necessary, removing the protecting group therefrom.

The compound of the formula (VII) to be used in the above-mentioned process may be prepared, for example, by oxidizing O-protected 5-acetyl-8-hydroxyquinoline with 80% m-chloroperbenzoic acid in a solvent (e.g., chloroform, methylene chloride, tetrahydrofuran, acetonitrile), and then heating the resultant O-protected 5-acetyl-8-hydroxyquinoline N-oxide in a solvent (e.g., acetic anhydride). Alternatively, the compound (VII) may be prepared by introducing a protecting group (Y') into 5-acetyl-8-hydroxycarbostyril (cf., Japanese patent publication (unexamined) No. 141879/1976) in a conventional manner.

Halogenation of the compound (VII) is preferably carried out in a solvent (e.g., chloroform, methylene chloride, tetrahydrofuran, methanol or a mixture thereof) at 20° to 60° C. under stirring. Suitable examples of the halogenating agent include N-bromosuccinimide, N-chlorosuccinimide, bromine or chlorine.

On the other hand, oxidation of the compound (VII) is preferably carried out at 20° to 100° C. in the presence of an oxidizing agent (e.g., selenium dioxide) in a solvent (e.g., dioxane, tetrahydrofuran or an aqueous mixture thereof).

The reaction of the compound (VIII) or (IX) with the compound (X) may be accomplished at 10° to 30° C. in a solvent (e.g., dimethylsulfoxide, dimethylformamide, chloroform, methanol, ethanol or a mixture thereof) under stirring. Further, the removal of the protecting group (Y') from the compound (II') or (III') may be carried out in the same manner as mentioned hereinbefore.

The compound (I) or an acid addition salt thereof shows potent bronchodilating activity and long-lasting therapeutic effect thereof, can produce selective stimulation of $\beta_2$-adrenoceptor and hence is useful for treatment or prophylaxis of various chronic obstructive pulmonary disease such as bronchial asthma or chronic bronchitis. For example, when estimated by the use of isolated tracheal chains of guinea pigs, the bronchodilating activity of 8-hydroxy-5-{(1R)-1-hydroxy-2-[N-((1R)-2-(p-methoxyphenyl)-1-methylethyl)-amino]ethyl}carbostyril of the present invention is about 10 and 100 times as strong as those of procaterol (chemical name; 8-hydroxy-5-[1-hydroxy-2-(isopropylamino)-butyl]carbostyril hydrochloride hemihydrate, J. Med. Chem., 20(8), 1103(1977)) and Isoproterenol (chemical name: 4-{1-hydroxy-2-[(1-methylethyl)amino]ethyl}-1,2-benzenediol hydrochloride), respectively. Moreover, since the compound (I) is characterized by the high potency ratio of the $\beta_2$-adrenoceptor stimulating action to the $\beta_1$-adrenoceptor stimulating action such as positive chronotropic action (e.g., increase in heart rate), said compound of the invention has particulary high safety for use as a bronchodilator. In addition, the toxicity of the compound (I) of the present invention is considerably low.

The carbostyril derivative (I) of the present invention can be used for pharmaceutical use in the form of either the free base or an acid addition salt thereof. Pharmaceutically acceptable acid addition salts of the carbostyril derivative (I) include, for example, salts thereof with an inorganic acid such as hydrochloric acid, hydrobromic acid, phosphoric acid, nitric acid or sulfuric acid, and an organic acid such as acetic acid, propionic acid, glycolic acid, lactic acid, malic acid, fumaric acid, malonic acid, succinic acid, aspartic acid, ascorbic acid, glutamic acid, nicotinic acid or methanesulfonic acid. Such pharmaceutically acceptable salts may be prepared, for example, by treating the free base of the compound (I) with a stoichiometrically equimolar amount of an acid.

The compound (I) and a salt thereof can be administered either orally or parenterally. The pharmaceutical preparation of the compound (I) may be either solid preparations such as tablets, pills, powders, capsules or granules, or liquid preparations such as solutions, suspensions or emulsions. Such preparations may be prepared in a conventional manner, for example, by admixing a compound (I) or a pharmaceutically acceptable salt thereof with a conventional carrier or diluent such as calcium carbonate, calcium phosphate, corn starch, potato starch, lactose, talc, and magnesium stearate. The daily dose of the compound (I) or a salt thereof may vary depending on the administration route, the age, weight or conditions of patients and the severity of diseases to be treated. In general, however, a preferred dose of said compound (I) or a salt thereof may be 0.01 to 30 μg, especially 0.01 to 3 μg, per kilogram of body weight per day.

Practical and presently-preferred embodiments of the present invention are illustratively shown in the following Examples.

EXPERIMENT 1

(Bronchodilating activity)

Isolated tracheal muscle preparations of Male Hartley guinea pigs (body weight: 430-645 g) were used to estimate the bronchodilating activity of a test compound according to Magnus' method. The preparation was suspended in an organ bath filled with 20 ml of Tyrode's solution (37° C.), and said solution was continuously bubbled with air. Histamine 2HCl was added to the bath (final concentration; $1 \times 10^{-5}$ g/ml) and the test compound was added thereto about 15 minutes after the addition of histamine 2HCl. Tension changes in the tracheal smooth muscle were recorded isometrically with a force-displacement transducer. Molar concentration of the test compound which produced 50% relaxation of the histamine-induced tracheal contraction were estimated from the concentration-response curve, and the potency ratio of the test compound to Isoproterenol was calculated therefrom. The result are shown in Table 1.

TABLE 1

| Test compounds | Potency ratio |
| --- | --- |
| Comp. No. 1 | 166 |
| Comp. No. 2 | 78 |
| Comp. No. 3 | 52 |
| Procaterol | 17 |
| Isoproterenol | 1 |

Note;
Comp. No. 1: 8-Hydroxy-5-{(1R)—1-hydroxy-2-[N—((1R)—2-(p-methoxypheny)-1-methylethyl)amino]ethyl}carbostyril hydrochloride
Comp. No. 2: 8-Hydroxy-5-{1-hydroxy-2-[N—(2-(p-methoxyphenyl)-1-methylethyl)amino]ethyl} carbostyril hydrochloride ($\alpha$-isomer obtained in Example 3 mentioned hereinafter)
Comp. No. 3: 8-Hydroxy-5-{1-hydroxy-2-[N—(2-(p-methoxyphenyl)-1-mehtylethyl)amino]ethyl} carbostyril hydrochloride (a mixture of $\alpha$- and $\beta$-isomers)
Chemical name of procaterol: 8-Hydroxy-5-[-hydroxy-2-(isopropylamino)butyl]carbostyril hydrochloride hemihydrate
Chemical name of Isoproterenol: 4-{1-hydroxy-2-[(1-methylethyl)amino]ethyl}-1,2-benzenediol hydrochloride.

EXPERIMENT 2

(Method)

Inhibitory effect on antigen-induced bronchoconstriction

Male Hartley guinea pigs (body weight: 280-520 g) were passively sensitized by intravenous injection of rabbit antiserum against ovalbumin (0.2 ml/100 g of body weight, PCA titer: $\times 1000$). 24 hours later, the animals were anesthetized with $\alpha$-chloralose (120 mg/kg. i.v.) and immobilized with gallamine triethiodide (5 mg/kg, i.v.) under artificial respiration. Lung volume changes were measured as overflow of air from the lung by the Konzett-Rössler method (cf. Arch. Exp. Pathol. Pharmakol., 195, 71 (1940)). The test compound was administered intravenously to the animals one minute before said animals were challenged with ovalbumin (30 µg/kg, i.v.). The $ED_{50}$ (i.e., the dose of the test compound which is necessary to produce 50% reduction of antigen-induced bronchoconstriction) was estimated from the dose-response curve.

Acute toxicity

A test compound was dissolved in 5% glucose solution, and the test compound solution (0.2 ml/10 g of body weight) was administered intravenously to Male ddY strain mice (body weight: 25-28 g). The $LD_{50}$ of the test compound was estimated by the Up and Down method.

(Results)

The results are shown in the following Table 2.

TABLE 2

| Test compounds* | Inhibitory effect on antigen-induced bronchoconstriction ($ED_{50}$) (µg/kg) | Acute toxicity ($LD_{50}$) (mg/kg) | Therapeutic index ($LD_{50}/ED_{50}$) |
| --- | --- | --- | --- |
| Comp. No. 1 | 0.09 | 84.6 | $9.4 \times 10^5$ |
| Comp. No. 2 | 0.18 | 91.3 | $5.1 \times 10^5$ |
| Procaterol | 0.64 | 70.3 | $1.1 \times 10^5$ |

Note;
*same as shown in the footnote of Table 1.

EXAMPLE 1

(1) 293 mg of 5-acetyl-8-benzyloxycarbostyril are dissolved in 15 ml of chloroform, and 200 mg of N-bromosuccinimide are added thereto. The mixture is refluxed for 2 hours under stirring. 300 mg of N-bromosuccinimide are added to the mixture and 4 hours after the commencement of the reaction, 100 mg of N-bromosuccinimide are further added thereto. Six hours after the reaction is started, the mixture is cooled and is allowed to stand at 20° C. for 2 days. Precipitated crystals are collected by filtration. Then, the crystals are washed with methanol and ether and then dried. 110 mg of 5-bromoacetyl-8-benzyloxycarbostyril are thereby obtained as colorless crystals. On the other hand, the filtrate is concentrated to dryness, and the residue is treated in the same manner as above, whereby 60 mg of 5-bromoacetyl-8-benzyloxycarbostyril are further recovered from the filtrate. Total yield: 170 mg (45.8%)

M.p. 203°-205° C. (decomp.) (recrystallized from methanol-chloroform)

Mass (m/e): 373, 371 (M+)

IR $\nu_{max}^{nujol}$ (cm$^{-1}$): 1675

NMR (d$_6$-DMSO) $\nu$: 4.85 (s 2H), 5.39 (s, 2H), 6.65 (d, J=10 Hz, 1H), 7.2-7.7 (m, 6H), 7.86 (d, J=9 Hz, 1H), 8.51 (d, J=10 Hz, 1H).

(2) 750 mg of 5-bromoacetyl-8-benzyloxycarbosytril are dissolved in 5 ml of dimethylsulfoxide, and 660 mg of N-(2-(p-methoxyphenyl)-1-methylethyl)amine are added thereto. The mixture is stirred at room temperature for 1.5 hours, whereby a mixture containing 8-benzyloxy-5-{1-oxo-2-[N-(2-(p-methoxyphenyl)-1-methylethyl)amino]ethyl}carbostyril is obtained. 10 ml of methanol and 380 mg of sodium borohydride are added to the mixture, and the mixture is further stirred at room temperature for one hour. The reaction mixture is extracted with chloroform, and the extract is washed with water, dried and then evaporated under reduced pressure to remove chloroform. The residue is purified by silica gel chromatography (solvent; chloroform:methanol=9:1), and then treated with an ethanol-hydrogen chloride solution. The crude product thus obtained is recrystallized from a mixture of isopropanol and ether. 210 mg of 8-benzyloxy-5-{1-hydroxy-2-[N-(2-(p-methoxyphenyl)-1-methylethyl)amino]ethyl}carbostyril monohydrochloride are obtained as colorless crystals. (a mixture of $\alpha$- and $\beta$-isomers) Yield: 21.2%

M.p. 193°-212° C.

Mass (m/e): 440 (M+—H$_2$O)

IR $\nu_{max}^{chloroform}$ (cm$^{-1}$): 1660

(3) 495 mg of 8-benzyloxy-5-{1-hydroxy-2-[N-(2-(p-methoxyphenyl)-1-methylethyl)amino]ethyl}carbostyril monohydrochloride are dissolved in a mixture of 26 ml of tetrahydrofuran and 4 ml of water, and 250 mg of 10% palladium-charcoal are added thereto. The mixture is stirred at room temperature for 1.5 hours under a hydrogen atmosphere. After the reaction, the mixture is filtered to remove catalyst, and a 10% methanolic hydrogen chloride solution is added to the filtrate. The mixture is concentrated under reduced pressure, and the residue is recrystallized from a mixture of isopropanol and ether. 350 mg of 8-hydroxy-5-{1-hydroxy-2-[N-(2-(p-methoxyphenyl-1-methylethyl)amino]ethyl}carbostyril dihydrochloride are obtained as colorless crystals. (a mixture of α- and β-isomers) Yield: 79.3%

M.p. 143°–154° C. (decomp.),
IR $\nu_{max}^{nujol}$ (cm$^{-1}$): 1640.

EXAMPLE 2

(1) 8.35 g of selenium dioxide are dissolved in 10 ml of water, and 250 ml of dioxane and 14.65 g of 5-acetyl-8-benzyloxycarbostyril are added thereto. The mixture is refluxed for 24 hours under stirring. After the reaction, 300 ml of dioxane is added to the mixture, and the mixture is filtered to remove inorganic materials. Inorganic materials are washed with 200 ml of methanol and 200 ml of dioxane. The filtrate and washings are combined and concentrated to about 200 ml under reduced pressure. 600 ml of water and 20 ml of 10% hydrochloric acid are added to the solution, and the solution is allowed to stand at 20° C. for 3 hours. Precipitated crystals are collected by filtration, washed with isopropanol-ether and n-hexane and then dried. 14.97 g of 8-benzyloxy-5-(dihydroxyacetyl)carbostyril ⅓ hydrate are obtained. Yield: 88.5% The product is recrystallized from a mixture of dioxane and water to give pale yellow needles.

M.p. 132°–147° C.
IR $\nu_{max}^{nujol}$ (cm$^{-1}$): 1655, 1682.

(2) 993 mg of 8-benzyloxy-5-(dihydroxyacetyl)carbostyril ⅓ hydrate are dissolved in 10 ml of dimethylsulfoxide, and 500 mg of N-(2-(p-methoxyphenyl)-1-methylethyl)amine are added thereto. The mixture is stirred at room temperature for 2 hours, whereby a reaction mixture containing 8-benzyloxy-5-{1-oxo-2-[N-(2-(p-methoxyphenyl)-1-methylethyl)imino]ethyl}carbostyril is obtained. The reaction mixture is ice-cooled, and 10 ml of methanol and 460 mg of sodium borohydride are added thereto. The mixture is stirred at room temperature for 2 hours. The reaction mixture is extracted with chloroform, and the extract is washed with water and 10% hydrochloric acid, dried and then evaporated under reduced pressure. The residue is recrystallized from a mixture of isopropanol and ether. 1010 mg of 8-benzyloxy-5-{1-hydroxy-2-[N-(2-(p-methoxyphenyl)-1-methylethyl)amino]ethyl}carbostyril monohydrochloride are obtained as colorless crystals (a mixture of α- and β-isomers). Yield: 68%

M.p. 193°–212° C.
Mass (m/e): 440 (M$^+$—H$_2$O)
IR $\nu_{max}^{chloroform}$ (cm$^{-1}$): 1660

(3) 8-Benzyloxy-5-{1-hydroxy-2-[N-(2-(p-methoxyphenyl)-1-methylethyl)amino]ethyl}carbostyril monohydrochloride is treated in the same manner as described in Example 1-(3), whereby 8-hydroxy-5-{1-hydroxy-2-[N-(2-(p-methoxyphenyl)-1-methylethyl)amino]ethyl}carbostyril dihydrochloride is obtained. (a mixture of α- and β-isomers).

EXAMPLE 3

(1) 2.65 g of 8-benzyloxy-5-(dihydroxyacetyl)carbostyril ⅓ hydrate, 1.65 g of N-(2-(p-methoxyphenyl)-1-methylethyl)amine, 30 ml of dimethylsufoxide, 760 mg of sodium borohydride and 20 ml of methanol are treated in the same manner as described in Example 2-(2). Then, the reaction mixture is extracted with ethyl acetate. The extract is ice-cooled under stirring, and 300 ml of an aqueous 3% sodium hydroxide solution are added thereto. A solution of 2.51 g of acetyl chloride in 10 ml of ethyl acetate is added dropwise to the mixture at 5°–10° C. The mixture is stirred at room temperature overnight. The ethyl acetate layer is washed with a saturated sodium bicarbonate solution and a saturated sodium chloride solution successively, dried and then evaporated under reduced pressure to remove ethyl acetate. The residue is chromatographed on the column of silica gel (solvent, chloroform:methanol=30:1), whereby the α- and β-isomers of 8-benzyloxy-5-{1-hydroxy-2-[N-(2-(p-methoxyphenyl)-1-methylethyl)-N-acetylamino]ethyl}carbostyril are obtained, respectively.

α-isomer: (i.e., a mixture of 8-benzyloxy-5-{(1R)-1-hydroxy-2-[N-((1R)-2-(p-methoxyphenyl)-1-methylethyl)-N-acetylamino]ethyl}carbostyril and 8-benzyloxy-5-{(1S)-1-hydroxy-2-[N-(1S)-2-(p-methoxyphenyl)-1-methylethyl)-N-acetylamino]ethyl}carbostyril), Yield: 640 mg (16%), colorless needles
M.p. 177°–180° C. (recrystallized from ethyl acetate)
Mass (m/e): 482 (M$^+$—H$_2$O)
IR $\nu_{max}^{nujol}$ (cm$^{-1}$): 1640, 3260, 3342
NMR (CDCl$_3$) δ: 1.28 (d, J=6.5 Hz, 3H), 1.82 (s, 3H), 2.66 (d, J=6.5 Hz, 2H), 3.77 (s, 3H), 5.19 (s, 2H), 6.6–7.4 (m, 7H), 7.4 (s, 5H), 8.35 (d, J=10.5 Hz, 1H).

β-isomer: (i.e., a mixture of 8-benzyloxy-5-{(1R)-1-hydroxy-2-[N-((1S)-2-(p-methoxyphenyl)-1-methylethyl)-N-acetylamino]ethyl}carbostyril and 8-benzyloxy-5-{(1S)-1-hydroxy-2-[N-((1R)-2-(p-methoxyphenyl)-1-methylethyl)-N-acetylamino]ethyl}carbostyril).

Yield: 1.805 g (45.1%), colorless prisms
M.p. 162°–163° C. (recrystallized from ethyl acetate)
Mass (m/e): 482 (M$^+$—H$_2$O)
IR $\nu_{max}^{nujol}$ (cm$^{-1}$): 1665, 3160, 3490
NMR (CDCl$_3$) δ: 1.18 (d, J=6.5 Hz, 3H), 1.91 (s, 3H), 2.5–2.8 (m, 2H), 3.76 (s, 3H), 5.17 (s, 2H), 6.5–7.35 (m, 7H), 7.39 (s, 5H), 8.42 (d, J=10.5 Hz, 1H)

(2-a). 500 mg of 8-benzyloxy-5-{1-hydroxy-2-[N-(2-p-methoxyphenyl-1-methylethyl)-N-acetylamino]ethyl}carbostyril (α-isomer) are added to a mixture of 15 ml of methanol and 6 g of an aqueous 5% sodium hydroxide solution. The mixture is refluxed for 5 hours under stirring. After the reaction, the mixture is evaporated under reduced pressure to remove methanol. The residue is acidified with 10% hydrochloric acid and extracted with chloroform. The extract is washed with water, dried and then evaporated under reduced pressure to remove chloroform. The residue is recrystallized from a mixture of isopropanol and ether. 470 mg of 8-benzyloxy-5-{1-hydroxy-2-[N-(2-(p-methoxyphenyl)-1-methylethyl)amino]ethyl}carbostyril monohydrochloride (α-isomer) are obtained as colorless needles. Yield: 95%

M.p. 200°–203° C.
Mass (m/e): 440 (M$^+$—H$_2$O)
IR $\nu_{max}^{nujol}$ (cm$^{-1}$): 1652, 2350–2750, 3280, 3405

(2-b). 750 mg of 8-benzyloxy-5-{1-hydroxy-2-[N-(2-(p-methoxyphenyl)-1-methylethyl)-N-acetylamino]ethyl}carbostyril (β-isomer) are treated in the same manner as described in paragraph (2-a). 680 mg of 8-benzyloxy-5-{1-hydroxy-2-[N-(2-(p-methoxyphenyl)-1-methylethyl)amino]ethyl}carbostyril monohydrochloride (β-isomer) are obtained as colorless needles. Yield: 91.6%

M.p. 217°–219° C. (recrystallized from isopropanol-ether)

Mass (m/e): 440 (M$^+$—H$_2$O)

IR $\nu_{max}^{nujol}$ (cm$^{-1}$): 3290, 3400.

(3-a). 247 mg of 8-benzyloxy-5-{1-hydroxy-2-[N-(2-(p-methoxyphenyl)-1-methylethyl)amino]ethyl}carbostyril monohydrochloride (α-isomer) are dissolved in a mixture of 5 ml of tetrahydrofuran and 1.5 ml of water, and 100 mg of 10% palladium-charcoal are added thereto. The mixture is stirred at room temperature under a hydrogen atmosphere for 1 hour. After the reaction, the mixture is filtered to remove catalyst, and 2 ml of a 10% methanolic hydrogen chloride solution is added to the filtrate. The mixture is condensed under reduced pressure, and the residue is recrystallized from a mixture of isopropanol and ether. 183 mg of 8-hydroxy-5-{1-hydroxy-2-[N-(2-(p-methoxyphenyl)-1-methylethyl)amino]ethyl}carbostyril dihydrochloride.½ hydrate (α-isomer) are obtained as colorless crystals. Yield: 82%

M.p. 154°–155° C. (decomp.)

IR $\nu_{max}^{nujol}$ (cm$^{-1}$): 1638, 3140, 3330

NMR (D$_2$O) δ: 1.36 (d, J=7 Hz, 3H), 2.92 (d, J=8 Hz, 2H), 3.32 (d, J=6 Hz, 2H), 3.77 (s, 3H), 5.45 (5, J=6 Hz, 1H), 6.62 (d, J=10 Hz, 1H), 6.80 (d, J=8 Hz, 2H), 6.95 (d, J=8 Hz, 1H), 7.10 (d, J=8 Hz, 2H), 7.20 (d, J=8 Hz, 1H), 8.08 (d, J=10 Hz, 1H).

Monohydrochloride: colorless prisms M.p. 213°–216° C. (decomp.) (recrystallized from methanol-water).

(3-b). 247 mg of 8-benzyloxy-5-{1-hydroxy-2-[N-(2-(p-methoxyphenyl)-1-methylethyl)amino]ethyl}carbostyril monohydrochloride (β-isomer) are treated in the same manner as described in paragraph (3-a). 175 mg of 8-hydroxy-5-{1-hydroxy-2-[N-(2-(p-methoxyphenyl)-1-methylethyl)amino]ethyl}carbostyril dihydrochloride (β-isomer) are obtained as colorless crystals. Yield: 79.5%

M.p. 161°–163° C. (decomp.) (recrystallized from isopropanol-ether)

IR $\nu_{max}^{nujol}$ (cm$^{-1}$): 1640, 3160, 3375

NMR (D$_2$O): 1.38 (d, J=6 Hz, 3H), 2.8–3.8 (m, 5H), 3.77 (s, 3H), 5.40 (q, J 8 Hz, 5 Hz, 1H), 6.62 (d, J=9 Hz, 1H), 6.81 (d, J=8 Hz, 2H), 6.96 (d, J=8 Hz, 1H), 7.11 (d, J=8 Hz, 2H), 7.19 (d, J=8 Hz, 1H), 8.07 (d, J=9 Hz, 1H).

EXAMPLE 4

(1) 4.60 g of 8-benzyloxy-5-{1-hydroxy-2-[N-(2-(p-methoxyphenyl)-1-methylethyl)amino]ethyl}carbostyril (α-isomer) are dissolved in 300 ml of chloroform, and 300 ml of an aqueous 5% potassium carbonate solution are added thereto. 3.6 g of (S)-1-(2-naphthylsulfonyl)pyrrolidine-2-carbonyl chloride are added dropwise to the mixture with stirring under ice-cooling, and the mixture is stirred at room temperature for 2 hours. The chloroform layer is collected, dried and then concentrated under reduced pressure to remove solvent. The residue is chromatographed on the column of silica gel (solvent, chlorofrm:methanol=49:1), whereby the following two compounds are obtained, respectively.

8-benzyloxy-5-{(1R)-1-hydroxy-2-[N-((1R)-2-(p-methoxyphenyl)-1-methylethyl)-N-((2S)-1-(2-naphthylsulfonyl)pyrrolidine-2-carbonyl)amino]ethyl}carbostyril Yield: 2.1 g (28.2%), colorless caramel, IR $\nu_{max}^{nujol}$ (cm$^{-1}$): 3390, 1650, 1605, Mass (m/e): 727 (M$^+$—H$_2$O)

8-benzyloxy-5-{(1S)-1-hydroxy-2-[N-((1S)-2-(p-methoxyphenyl)-1-methylethyl)-N-((2S)-1-(2-naphthylsulfonyl)pyrrolidine-2-carbonyl)amino]ethyl}carbostyril Yield: 2.2 of (29.5%), colorless caramel IR $\nu_{max}^{nujol}$ (cm$^{-1}$): 3390, 1650, 1605

Mass (m/e): 727 (M$^+$—H$_2$O)

(2-a). 2.61 g of 8-benzyloxy-5-{(1R)-1-hydroxy-2-[N-((1R)-2-(p-methoxyphenyl)-1-methylethyl)-N-((2S)-1-(2-naphthylsulfonyl)-pyrrolidine-2-carbonyl)amino]ethyl}carbostyril are dissolved in 100 ml of methanol, and 35 ml of 1N potassium hydoxide-methanol and 10 ml of water are added thereto. The mixture is refluxed for 3 hours with stirring. The mixture is concentrated under reduced pressure to remove solvent. The residue is extracted with chloroform, and the extract is washed with 5% hydrochloric acid, dried and then concentrated under reduced pressure to remove solvent. The residue is recrystallized from a mixture of isopropanol and water. 1.1 g of 8-benzyloxy-5-{(1R)-1-hydroxy-2-[N-((1R)-2-(p-methoxyphenyl)-1-methylethyl)amino]ethyl}carbostyril hydrochloride are obtained as colorless prisms. Yield: 63.6%

M.p. 203°–205° C. (decomp.)

Free base:

M.p. 130.5°–132.5° C.

$[\alpha]_D^{20}$ —45.31° (c=1.05, methanol)

IR $\nu_{max}^{nujol}$ (cm$^{-1}$): 3340, 3160, 1640

Mass (m/e): 440 (M$^+$—H$_2$O)

NMR (CDCl$_3$) ν: 1.08 (d, J=6.7 Hz, 3H), 2.5–3.0 (m, 5H), 3.76 (s, 3H,), 4.8–5.10 (m, 1H), 5.14 (s, 2H), 6.5–7.3 (m, 7H), 7.39 (s, 5H), 8.05 (d, J=9.6 Hz, 1H).

(2-b). 2.61 g of 8-benzyloxy-5-{(1S)-1-hydroxy-2-[N-((1S)-2-(p-methoypheyl)-1-methylethyl)-N-((2S)-1-(2-naphthylsulfonyl)-pyrrolidine-2-carbonyl)amino]ethyl}carbostyril are dissolved in 100 ml of methanol, and 35 ml of 1N potassium hydroxide-methanol and 10 ml of water are added thereto. The mixture is refluxed for 3 hours with stirring. The mixture is concentrated under reduced pressure to remove solvent. The residue is extracted with chloroform, and the extract is dried and concentrated under reduced pressure to remove solvent. The residue is recrystallized twice from ethyl acetate. 1.1 g of 8-benzyloxy-5-{(1S)-1-hydroxy-2-[N-((1S)-2-(p-methoxyphenyl)-1-methylethyl)amino]ethyl} carbostyril are obtained as colorless needles. Yield: 68.8%

M.p. 130.5°–132° C.

$[\alpha]_D^{20}$ +40.9° (c=1.0, chloroform)

IR $\nu_{max}^{nujol}$ (cm$^{-1}$): 3340, 3160, 1640

Mass (m/e): 458 (M$^+$), 440 (M$^+$—H$_2$O)

NMR (CDCl$_3$) δ: 1.08 (d, J=6.7 Hz, 3H), 2.5–3.0 (m, 5H), 3.76 (s, 3H), 4.8–5.10 (m, 1H), 5.14 (s, 2H), 6.5–7.3 (m, 7H), 7.39 (s, 5H), 8.05 (d, J=9.6 Hz, 1H).

(3-a). A mixture of 3.5 g of 8-benzyloxy-5-{(1R)-1-hydroxy-2-[N-((1R)-2-(p-methoxyphenyl)-1-methylethyl)amino]ethyl}carbostyril hydrochloride, 240 mg of 10% palladium-charcoal, 100 ml of tetrahydrofuran and 10 ml of water is shaken at room temperature at an atmospheric pressure under a hydrogen atmosphere for 2 hours. Insoluble materials are collected by filtration and washed with an aqueous 10% ethanol solution. The filtrate and washings are combined, and the combined solution is concentrated under reduced pressure to remove solvent. The residue is crystallized with a mixture of ethanol, water and isopropyl ether, and crystalline precipitates are collected by filtration. 2.38 g of 8-hydroxy-5-{(1R)-1-hydroxy-2-[N-((1R)-2-(p-methoxyphenyl)-1-methylethyl)amino]ethyl}carbostyril hydrochloride are obtained as colorless crystals. Yield: 83%

M.p. 170.0°–171.5° C. (decomp.)
$[\alpha]_D^{22} -64.40°$ (c=1.00, methanol)
IR $\nu_{max}^{nujol}$ (cm$^{-1}$): 3300 (broad), 1640, 1610, 1600
NMR (D$_2$O) δ: 1.36 (d, J=7 Hz, 3H), 2.92 (d, J=8 Hz, 2H), 3.32 (d, J=6 Hz, 2H), 3.77 (s, 3H), 5.45 (t, J=6 Hz, 1H), 6.62 (d, J=10 Hz, 1H), 6.80 (d, J=8 Hz, 2H), 6.95 (d, J=8 Hz, 1H), 7.10 (d, J=8 Hz, 2H), 7.20 (d, 8 Hz, 1H), 8.08 (d, J=10 Hz, 1H).

(3-b). A mixture of 916 mg of 8-benzyloxy-5-{(1S)-1-hydroxy-2-[N-((1S)-2-(p-methoxyphenyl)-1-methylethyl)amino]ethyl}carbostyril, 100 mg of 10% palladium-charcoal, 2 ml of 1N hydrochloric acid and 20 ml of tetrahydrofuran is shaken at room temperature at an atmospheric pressure under a hydrogen atmosphere for 2 hours. Insoluble materials are collected by filtration and washed with an aqueous 10% ethanol solution. The filtrate and washings are combined, and the combined solution is concentrated under reduced pressure to remove solvent. The residue is crystallized with a mixture of methanol and ether, and crystalline precipitates are collected by filtration. 623 mg of 8-hydroxy-5-{(1S)-1-hydroxy-2-[N-((1S)-2-(p-methoxyphenyl)-1-methylethyl)amino]ethyl}carbostyril hydrochloride are obtained as colorless crystals. Yield: 77%

M.p. 166°–167° C. (decomp.)
$[\alpha]_D^{20} +65.5°$ (c=1.0, methanol)
IR $\nu_{max}^{nujol}$ (cm$^{-1}$): 3390, 3320, 1640, 1610, 1600

The Mass and NMR data of this product are identical with those of the product obtained in the above-mentioned paragraph (3-a).

EXAMPLE 5

(1) 330 mg of 8-benzyloxy-5-(dihydroxyacetyl)carbostyril ⅓ hydrate, 165 mg of (R)-N-(2-(p-methoxyphenyl)-1-methylethyl)amine, 7 ml of dimethylsulfoxide, 7 ml of methanol and 38 mg of sodium borohydride are treated in the same manner as described in Example 2-(2) except that the reduction reaction is conducted at 0° to 10° C. Then, the reaction mixture is extracted with ethyl acetate. The extract is washed with water, dried and then concentrated under reduced pressure to remove solvent. 10 ml of ethyl acetate and 10 ml of an aqueous 10% potassium carbonate solution are added to the residue, and 0.5 ml of acetyl chloride are added to the mixture with stirring under ice-cooling. The mixture is stirred at the same temperature for 30 minutes. The ethyl acetate layer is collected and washed with water and a saturated sodium chloride solution, successively. The ethyl acetate solution is dried and concentrated under reduced pressure to remove solvent. The residue is chromatographed on the column of silica gel (solvent, methanol:chloroform=1:19), whereby the following two compounds are obtained, respectively.

8-benzyloxy-5-{(1R)-1-hydroxy-2-[N-((1R)-2-(p-methoxyphenyl)-1-methylethyl)-N-acetylamino]ethyl}carbostyril Yield: 50 mg (10%), colorless caramel
Mass (m/e): 482 (M$^+$—H$_2$O)

8-benzyloxy-5-{(1S)-1-hydroxy-2-[N-((1R)-2-(p-methoxyphenyl)-1-methylethyl)-N-acetylamino]ethyl}carbostyril Yield: 410 mg (82%), colorless carmel
Mass (m/e): 482 (M$^+$—H$_2$O)

(2) 8-benzyloxy-5-{(1R)-1-hydroxy-2-[N-((1R)-2-(p-methoxyphenyl)-1-methylethyl)-N-acetylamino]ethyl}carbostyril is treated in the same manner as described in Example 3-(2-a) and (3-a), whereby 8-hydroxy-5-{(1R)-1-hydroxy-2-[N-((1R)-2-(p-methoxyphenyl)-1-mthylethyl)amino]ethyl}carbostyril hydrochloride is obtained.

EXAMPLE 6

8-benzyloxy-5-{(1R)-1-hydroxy-2-[N-((1R)-2-(p-methoxyphenyl)-1-methylethyl)-N-(p-nitrobenzoyl)amino]ethyl}carbostyril is obtained in the same manner as described in Example 5-(1). A mixture of 3.7 g of 8-benzyloxy-5-{(1R)-1-hydroxy-2-[N-((1R)-2-(p-methoxyphenyl)-1-methylethyl)-N-(p-nitrobenzoyl)amino]ethyl}carbostyril, 100 ml of 96% potassium hydroxide-ethanol and 10 ml of water is refluxed for one hour under stirring. The mixture is concentrated under reduced pressure to remove solvent. The residue is extracted with chloroform, and the extract is washed with water, 10% hydrochloric acid and a saturated sodium chloride solution, successively. The chloroform solution is dried and concentrated under reduced pressure to remove solvent. The residue is recrystallized from an aqueous 10% isopropanol solution. 1.85 g of 8-benzyloxy-5-{(1R)-1-hydroxy-2-[N-((1R)-2-(p-methoxyphenyl)-1-methylethyl)amino]ethyl}carbostyril hydrochloride are obtained as colorless prisms. Yield: 65%

The physico-chemical properties of this product are identical with those of the product obtained in Example 4-(2-a).

(3) 8-benzyloxy-5-{(1R)-1-hydroxy-2-[N-((1R)-2-(p-methoxyphenyl)-1-methylethyl)amino]ethyl}carbostyril hydrochloride is treated in the same manner as described in Example 4-(3-a), whereby 8-hydroxy-5-{(1R)-1-hydroxy-2-[N-((1R)-2-(p-methoxyphenyl)-1-methylethyl)amino]ethyl}carbostyril hydrochloride is obtained.

EXAMPLE 7

(1) 10 g of 8-benzyloxy-5-(dihydroxyacetyl)carbostyril ⅓ hydrate, 5 g of (R)-N-(2-(p-methoxyphenyl)-1-methylethyl)amine, 100 ml of dimethylsulfoxide, 100 ml of methanol and 1.15 g of sodium borohydride are treated in the same manner as described in Example 2-(2). Then, the reaction mixture is extracted with ethyl acetate. The extract is concentrated under reduced pressure to remove solvent. 250 ml of ethyl acetate and a slution of 8.36 g of potassium carbonate in 70 ml of water are added to the residue, and 3.76 g of chloroacetyl chloride are added dropwise thereto at 5° to 7° C. under stirring. The ethyl acetate layer is collected and washed with water and a saturated sodium chloride solution, successively. The ethyl acetate solution is dried and concentrated under reduced pressure to remove solvent. The residue is dissolved in 80 ml of hot methanol, and the solution is allowed to stand at room temperature. Crystalline precipitates are collected by filtration. 10.2 g of 8-benzyloxy-5-{(1S)-1-hydroxy-2-[N-((1R)-2-(p-methoxyphenyl)-1-methylethyl)-N-chloroacetylamino]ethyl}carbostyril hemihydrate are obtained as colorless needles. Yield: 61.9%

M.p. 109°–114° C.

Mass (m/e): 516 (M+—H₂O)

[α]$_D^{20}$ −106.83° (c=1.02, chloroform)

(2) 7.12 g of 8-benzyloxy-5-{(1S)-1-hydroxy-2-[N-((1R)-2-(p-methoxyphenyl)-1-methylethyl)-N-chloroacetylamino]ethyl}carbostyril hemihydrate are dissolved in a mixture of 70 ml of chloroform and 70 ml of methanol, and the solution is concentrated under reduced pressure to remove solvent. The residue is dissolved in 70 ml of methylene chloride, and 2.38 g of thionyl chloride are added thereto at 5° to 7° C. The mixture is stirred at the same temperature for one hour. Then, the mixture is concentrated under reduced pressure to remove solvent. The residue is dissolved in 70 ml of dioxane, and 15 ml of water are added thereto at room temperature. The mixture is stirred at the same temperature for one hour. A solution of 9.3 g of 96% potassium hydroxide in a mixture of 50 ml of water and 50 ml of methanol is added to the mixture, and the mixture is stirred for 20 minutes. The mixture is concentrated under reduced pressure to remove solvent. The residue is extracted with ethyl acetate, and the extract is washed with water and a saturated sodium chloride solution, successively. The ethyl acetate solution is dried and concentrated under reduced pressure to remove solvent. The residue is recrystallized from a mixture of ethyl acetate benzene. 4.13 g of 8-benzyloxy-5-{(1R)-1-hydroxy-2-[N-((1R)-2-(p-methoxyphenyl)-1-methylethyl)amino]ethyl}carbostyril are obtained as colorless needles.

Yield: 67.7%

The physico-chemical properties of this product are identical with those of the product obtained in Example 4-(2-a).

(3) 8-benzyloxy-5-{(1R)-1-hydroxy-2-[N-((1R)-2-(p-methoxyphenyl)-1-methylethyl)amino]ethyl}carbostyril is treated in the same manner as described in Example 4-(3-a), whereby 8-hydroxy-5-{(1R)-1-hydroxy-2-[N-((1R)-2-(p-methoxyphenyl)-1-methylethyl)amino]ethyl}carbostyril is obtained.

EXAMPLE 8

(1) 2 g of 8-benzyloxy-5-{1-hydroxy-2-[N-(2-(p-methoxyphenyl)-1-methylethyl)-N-acetylamino]ethyl}carbostyril (β-isomer) are dissolved in 25 ml of methylene chloride, and 960 mg of thionyl chloride are added thereto at 5° to 10° C. The mixture is stirred at 10° to 15° C. for one hour. Then, the mixture is concentrated under reduced pressure to remove excess thionyl chloride and methylene chloride. The reside is dissolved in 80 ml of water, and the solution is allowed to stand at room temperature for 4 hours. The solution is concentrated under reduced pressure to remove water. The residue is crystallized with a mixture of water and tetrahydrofuran, and the resultant crystals are recrystallized from a mixture of methanol, chloroform and ether. 1.6 g of 8-benzyloxy-5-{1-acetoxy-2-[N-(2-(p-methoxyphenyl)-1-methylethyl)amino]ethyl}carbostyril (α-isomer) hydrochloride.methanol are obtained as colorless prisms. Yield: 70.3%

M.p. 175°–178° C. (decomp.)

Mass (m/e): 501 (M+1)+, 500 (M+), 499 (M−1)+, 400 (M+, —CH₃COOH)

IR $\nu_{max}^{nujol}$ (cm⁻¹): 3350, 2400–2150, 1740, 1673

Free base:

NMR(CDCl₃)ν: 1.08 (d, J=6.5 Hz, 3H), 1.94 (s, 3H), 2.4–3.3 (m, 5H), 3.74 (s, 3H), 5.14 (s, 2H), 6.14 (q, J=5.8 Hz, 1H), 6.6–7.1 (m, 7H), 7.26(s, 5H), 8.06 (d, J=10 Hz, 1H), (2) 0.5 g of 8-benzyloxy-5-{1-acetoxy-2-[N-(2-(p-methoxyphenyl)-1-methylethyl)amino]ethyl}carbostyril (α-isomer) hydrochloride.methanol is dissolved in a mixture of 10 ml of methanol and 2 ml of water, and 180 mg of triethylamine are added thereto. The mixture is refluxed for 5 hours under stirring. The mixture is concentrated under reduced pressure to remove solvent. The residue is extracted with chloroform, and the extract is washed with 5% hydrochloric acid. The chloroform solution is dried and concentrated under reduced pressure to remove solvent. The residue is recrystallized from a mixture of isopropanol and ether. 365 mg of 8-benzyloxy-5-{1-hydroxy-2-[N-(2-(p-methoxyphenyl)-1-methylethyl)amino]ethyl}carbostyril (α-isomer) hydrochloride are obtained. Yield: 86.1%

The physico-chemical properties of this product are identical with those of the product obtained in Example 3-(2-a).

(3) 8-benzyloxy-5-{1-hydroxy-2-[N-2-(p-methoxyphenyl)-1-methylethyl)amino]ethyl}carbstyril (α-isomer) hydrochloride is treated in the same manner as described in Example 3-(3-a), whereby 8-hydroxy-5-{1-hydroxy-2-[N-(2-(p-methoxyphenyl)-1-methylethyl)amino]ethyl}carbotyril (α-isomer) hydrochloride is obtained.

EXAMPLE 9

(1) 100 mg of 8-benzyloxy-5-{1-hydroxy-2-[N-2-(p-methoxyphenyl)-1-methylethyl)-N-acetylamino]ethyl}carbostyril (β-isomer) are dissolved in 2 ml of methylene chloride, and 35.7 mg of thionyl chloride are added thereto under ice-cooling. The mixture is stirred for 15 minutes. After the reaction, the mixture is concentrated under reduced pressure. 4 ml of dioxane are added to the residue. The mixture is ice-cooled and 75 mg of potassium acetate are added thereto. The mixture is stirred at room temperature for 15 minutes. 40 mg of sodium hydroxide are added to the mixture, and the mixture is stirred at room temperature for 0.5 hour. After the reaction, the mixture is extracted with ethyl acetate. 5 ml of an aqueous 5% sodium hydroxide solution are added to the organic layer. The mixture is stirred under cooling and treated with 45 mg of acetyl chloride. After the reaction, the organic layer is collected, washed with water, dried and then evaporated under reduced pressure to remove ethyl acetate. The residue is recrystallized from ethyl acetate. 80 mg of 8-benzyloxy-5-{1-hydroxy-2-[N-(2-(p-methoxyphenyl)-1-methylethyl)-N-acetylamino]ethyl}carbostyril (α-isomer) are obtained as colorless needleds. Yield: 80%

M.p. 177°–180° C.

IR-spectrum and Rf-value of the product are identical with those of the product obtained in Example 3-(1).

(2) 8-Benzyloxy-5-{1-hydroxy-2-[N-(2-(p-methoxyphenyl)-1-methylethyl)-N-acetylamino]ethyl}carbostyril (α-isomer) is converted to the corresponding β-isomer in the same manner as described above.

EXAMPLE 10

(1) 10.84 g of 8-benzyloxy-5-(dihydroxyacetyl)carbostyril ⅓ hydrate and 5.66 g of N-(2-(p-methoxyphenyl)-1-methylethyl)amine are dissolved in 100 ml of dimethylsulfoxide, and the solution is stirred at room temperature for one hour. The mixture is extracted with chloroform, and the extract is washed with water and a saturated sodium chloride solution, successively. The chloroform solution is dried and concentrated under reduced pressure to remove solvent. The residue is crystallized with a mixture of ethyl acetate and n-hexane, and crystalline precipitates are collected by filtration. 13 g of 8-benzyloxy-5-{1-oxo-2-[N-(2-(p-methoxyphenyl)-1-methylethyl)imino]ethyl}carbostyril are obtained as yellow solid. Yield: 87.6%

M.p. 151°-152° C.

Mass (m/e): 454 (M+)

IR $\nu_{max}^{nujol}$ (cm$^{-1}$): 1660, 1650

NMR(CDCl$_3$)$\nu$: 1.32 (d, J=7 Hz, 3H), 2.8-2.9 (m, 2H), 3.77 (s, 3H0, 5.24 (s, 3H), 6.70 and 8.58 (1H each, d, J=10 Hz), 6.79 and 7.04 (2H each, d, J=9 Hz), 6.91 and 7.36 (1H each, d, J=9 Hz), 7.40 (s, 5H), 7.78 (s, 1H)

(2) 8-benzyloxy-5-{1-oxo-2-[N-(2-(p-methoxyphenyl)-1-methylethyl)imino]ethyl}carbostyril is treated in the same manner as described in Example 2-(2) and (3), whereby 8-hydrxy-5-{1-hydroxy-2-[N-(2-(p-methoxyphenyl)-1-methylethyl)amino ethyl carbostyril is obtained. (a mixture of α- and β-isomers)

EXAMPLE 11

(1) One g of 8-benzyloxy-5-(dihydroxyacetyl)carbostiril ⅓ hydrate and 520 mg of (R)-N-(2-(p-methoxyphenyl)-1-methylethyl)amine are dissolved in 10 ml of dimethylsulfoxide, and the solution is stirred at room temperature for one hour. After the reaction is completed, the mixture is treated in the same manner as described in Example 10-(1). 1.06 g of 8-benzyloxy-5-{1-oxo-2-[N-((1R)-2-(p-methoxyphenyl)-1-methylethyl)imino]ethyl}carbostyril are obtained as pale yellow scales. Yield: 75%

M.p. 114°-116° C.

$[\alpha]_D^{20} - 97.5°$ (c=1.06, methanol)

IR$\nu_{max}^{nujol}$ (cm$^{-1}$): 1670, 1625

The Mass and NMR data of this product are identical with those of the product obtained in Example 10-(1).

(2) 8-benzyloxy-5-{1-oxo-2-[N-((1R)-2-(p-methoxyphenyl)-1-methylethyl)imino]ethyl}carbostyril is treated in the same manner as described in Example 2-(2) and Example 5, whereby 8-hydroxy-5-{(1R)-1-hydroxy-2-[N-((1R)-2-(p-methoxyphenyl)-1-methylethyl)amino]ethyl}carbostyril hydrochloride is obtained.

EXAMPLE 12

(1) A solution of 1.65 g of (R)-N-(2-(p-methoxyphenyl)-1-methylethyl)amine in 5 ml of dimethylsulfoxide is added to a solution of 3.3 g of 8-benzyloxy-5-(dihydroxyacetyl)carbostyril ⅓ hydrate in 45 ml of dimethylsulfoxide, and the mixture is stirred at room temperature for 30 minutes. 60 ml of methanol are added to the mixture under ice-cooling, and 0.39 g of sodium borohydride is added thereto at 5° to 10° C. The mixture is stirred at the same temperature for 15 minutes. The mixture is concentrated under reduced pressure to remove solvent. The residue is extracted with ethyl acetate, and the extract is washed with water and a saturated sodium chloride solution, successively. The ethyl acetate solution is dried and concentrated under reduced pressure to remove solvent. The residue is converted to its hydrochloride, and the hydrochloride is crystallized with a mixture of isopropanol and and ethyl acetate. The resultant crystals are recrystallized 3 times from ethanol. 2.28 g of 8-benzyloxy-5-{(1S)-1-hydroxy-2-[N-((1R)-2-(p-methoxyphenyl)-1-methylethyl)amino]ethyl}carbostyril hydrochloride ⅛ ethanol hemihydrate are obtained as colorless needles. Yield: 46%

M.p. 164.5°-167° C.

$[\alpha]_D^{20} + 9.60°$ (c=1.0, methanol)

Mass (m/e): 440 (M$^+$—H$_2$O))

IR $\nu_{max}^{nujol}$ (cm$^{-1}$): 3405, 3350, 3200, 2740-2450, 1650, 1605.

NMR(d$_6$-DMSO): 1.15 (d, J=8 Hz, 3H), 2.4-2.8 (m, 2H, 2.82-3.9 (m, 4H), 3.72 (s, 3H), 4.36 (broad s, 1H), 5.33 (s, 2H), 6.58 (d, J=10 Hz, 1H), 6.86 (d, J=9 Hz, 2H), 7.14 (d, J=9 Hz, 2H), 8.36 (d, J=10 Hz, 1H), 6.8-7.7 (m, 7H)

(2) 8-benzyloxy-5-{(1S)-1-hydroxy-2-[N-((1R)-2-(p-methoxyphenyl)-1-methylethyl)amino]ethyl}carbostyril hydrochloride is treated in the same manner as described in Example 4-(3-a), whereby 8-hydroxy-5-{(1S)-1-hydroxy-2-[N-((1R)-2-(p-methoxyphenyl)-1-methylethyl)amino]ethyl}carbostyril is obtained.

EXAMPLE 13

(1) A solution of 7.8 g of bromine in 30 ml of methylene chloride is added dropwise to a refluxing solution of 13 g of 5-acetyl-8-benzyloxycarbostyril and 7.56 g of boron trifluoride etherate in 170 ml of methylene chloride, and the mixture is refluxed for 30 minutes under heating. The mixture is concentrated under reduced pressure to remove solvent. The residue is made alkaline with an aqueous 10% potassium carbonate solution, and the resultant precipitates are collected by filtration. The crystals are recrystallized from a mixture of chloroform and methanol. 12.51 g of 5-bromoacetyl-8-benzyloxycarbostyril are obtained as pale yellow needles. Yield: 75.7%

The physico-chemical properties of this product are identical with those of the product obtained in Example 1-(1).

(2) A mixture of 3.72 g of 5-bromoacetyl-8-benzyloxycarbostyril, 3.3 g of N-(2-(p-methoxyphenyl)-1-methylethyl)amine, 2.6 g of sodium bicarbonate, 10 ml of methylene chloride and 2 ml of dimethylformamide is refluxed for 30 minutes under stirring. The mixture is concentrated under reduced pressure to remove solvent. The residue is extracted with chloroform, and the extract is washed with 10% hydrochloric acid, dried and then concentrated under reduced pressure to remove solvent. The residue is rcrystallized form a mixture of ethanol and isopropanol: 3.53 g of 8-benzyloxy-5-{1-oxo-2-[N-(2-(p-methoxypheyl)-1-methylethyl)amino]ethyl}carbostyril hydrochloride are obtained as colorless needles. Yield: 71.6%

M.p. 201.5°-208° (decomp.)

Mass (m/e): 456 (M+), 335, 121

IR$\nu_{max}^{nujol}$ (cm$^{-1}$): 3380, 1690, 1660.

(3) 8-benzyloxy-5-{1-oxo-2-[N-(2-(p-methoxyphenyl)-1-methylethyl)amino]ethyl}carbostyril hydrochloride is treated in the same manner as described in Example 1-(2) and (3), whereby 8-hydroxy-5-{1-hydroxy-2-[N-(2-(p-methoxyphenyl)-1-methylethyl)amino]ethyl}carbostyril dihydrochloride is obtained. (a mixture of α- and β-isomers)

(PREPARATION OF STARTING COMPOUNDS)

Preparation 1

(1) 27 g of 5-acetyl-8-hydroxyquinoline hydrochloride are dissolved in 540 ml of anhydrous dimethylformamide and 50 g of powdered potassium carbonate are added thereto. 18.4 g of benzyl chloride are added to the mixture at 50° C. under an argon atmosphere, and the mixture is stirred at the same temperature for 4.5 hours and then further stirred at room temperature for 1.5 hours. After the reaction, water is added to the mixture, and the aqueous mixture is extracted with ethyl acetate. The extract is washed with water, a saturated sodium chloride solution, dried and then evaporated under reduced pressure to remove ethyl acetate. The residue is recrystallized from ethanol. 19.1 g of 5-acetyl-8-benzyloxyquinoline are obtained as brownish prisms. 6.35 g of said product are further recovered from the mother liquor.

Total yield: 25.5 g (76.1%) M.p. 131°–133° C.

(2) 5 g of 5-acetyl-8-benzyloxyquinoline are dissolved in 50 ml of chloroform. The solution is ice-cooled and 3.12 g of 80% m-chloroperbenzoic acid are added thereto under stirring. The mixture is stirred at room temperature for 24 hours and at 50° C. for 7.5 hours. The mixture is then stirred at room temperature for 64 hours. 2 g of 80% m-chloroperbenzoic acid are further added to the mixture during the reaction. After the reaction, chloroform is added to the mixture. The mixture is washed with water, a 4% sodium bicarbonate solution and a saturated sodium chloride solution, dried and then evaporated under reduced pressure to remove chloroform. 5-Acetyl-8-benzyloxyquinoline-N-oxide is obtained as yellow solid.

M.p. 136.5°–137.5° C. (recrystallized from acetone)

The yellow product obtained above is dissolved in 60 ml of acetic anhydride, and the solution is stirred at 100° C. for 8.5 hours. After the reaction, the mixture is evaporated under reduced pressure and the residue is recrystallized from methanol. 1.95 g of 5-acetyl-8-benzyloxycarbostyril are obtained as pale brownish prisms. 1.06 g of said product is further recovered from the mother liquor. Total yield: 3.01 g (56.8%)

M.p. 174°–176° C.

Preparation 2

15.23 g of 5-acetyl-8-hydroxycarbostyril and 15.7 g of benzyl chloride are added to a mixture of 200 ml of acetone and 90 ml of water, and 10.35 g of potassium carbonate are added thereto. The mixture is refluxed for 12 hours under stirring. Then, the mixture is evaporated under reduced pressure to remove acetone, and the residue is extracted with chloroform. The extract is washed with water, dried and evaporated under reduced pressure to remove chloroform. The residue is recrystallized from a mixture of ethyl acetate and n-hexane. 10.14 g of 5-acetyl-8-benzyloxycarbostyril are obtained as prisms. 1.58 g of said product are further recovered from the mother liquor.

Total yield: 11.72 g (53.3%)

Preparation 3

(1) 19.3 g of α-methyl-α-nitro-p-methoxystyrene are dissolved in a mixture of 180 ml of methanol and 60 ml of tetrahydrofuran, and 11.4 g of sodium borohydride are added thereto under ice-cooling. The mixture is stirred at room temperature overnight. 3 g of 10% palladium-charcoal and 30 ml of methanol, are added to the mixture, and the mixture is shaken at room temperature at an atmospheric pressure under a hydrogen atmosphere for 9 hours. Insoluble materials are filtered off, and the filtrate is concentrated under reduced pressure to remove solvent. The residue is extracted with chloroform, and the extract is dried and concentrated under reduced pressure to remove solvent. 15.5 g of N-(2-(p-methoxyphenyl)-1-methylethyl)amine are obtained as colorless oil. Yield: 94.4% B.p. 110°–115° C./5 mmHg (2) 81.7 g of N-(2-(p-methoxyphenyl)-1-methylethyl)amine and 150 g of (S)-1-(2-naphthylsulfonyl)pyrrolidine-2-carboxylic acid are dissolved in 1000 ml of methanol and the solution is concentrated under redued pressure to remove methanol. The residue is recrystallized twice from a mixture of ethyl acetate and isopropanol (1:1), once from isopropanol, twice from a mixture of isopropanol and ethanol (1:1) and then from a mixture of isopropanol and ethanol (1:2). 57.56 g of a salt of (R)-N-(2-(p-methoxyphenyl)-1-methylethyl)amine with (S)-1-(2-naphthylsulfonyl)pyrrolidine-2-carboxylic acid are obtained as colorless needles.

M.p. 163.5°–167° C.

The above-obtained salt (57.56 g) is converted to its free base by using an aqueous potassium carbonate, and the free base is distilled under reduced pressure. 14.22 g of (R)-N-(2-(p-methoxyphenyl)-1-methylethyl)amine are obtained as colorless oil. Yield: 35%

B.p. 90°–95° C./2 mmHg

Hydrochloride:

M.p. 252°–254° C. (decomp.)

$[\alpha]_D^{25} -23.2°$ (c=2.0, water).

What we claim is:

1. A carbostyril compound of the formula:

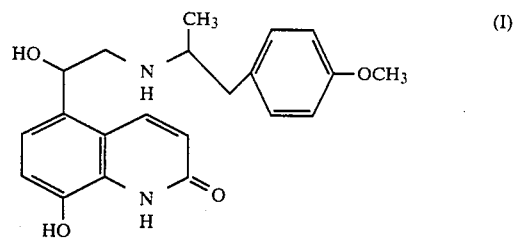

or a pharmaceutically acceptable acid addition salt thereof.

2. The compound of claim 1 which is a mixture of 8-hydroxy-5-{(1R)-1-hydroxy-2-[N-((1R)-2-(p-methoxyphenyl)-1-methylethyl)amino]ethyl}carbostyril and 8-hydroxy-5-{(1S)-1-hydroxy-2-[N-((1S)-2-(p-methoxyphenyl)-1-methylethyl)amino]ethyl}carbostyril, or a pharmaceutically acceptable acid addition salt thereof.

3. The compound of claim 1 which is 8-hydroxy-5-{(1R)-1-hydroxy-2-[N-((1R)-2-(p-methoxyphenyl)-1-methylethyl)amino]ethyl}carbostyril or a pharmaceutically acceptable acid addition salt thereof.

4. A pharmaceutical composition which comprises a therapeutically effective amount of a bronchodilating compound of the formula:

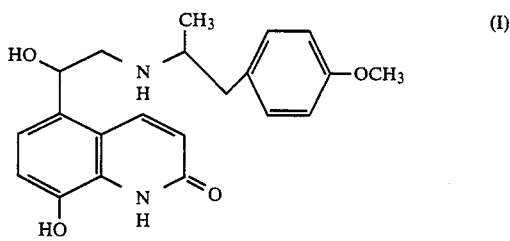

or a pharmaceutically acceptable acid addition salt thereof, and a pharmaceutically acceptable carrier therefor.

5. A method of producing a bronchodilating effect on a warm-blooded animal comprising administering to said warm-blooded animal an effective amount of a compound of the formula:
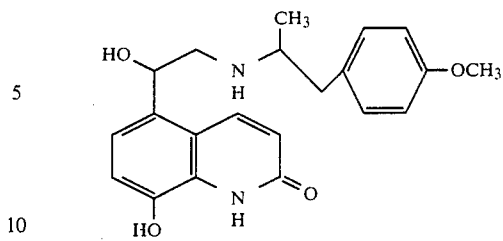
or a pharmaceutically acceptable acid addition salt thereof.
* * * * *